United States Patent [19]   [11] Patent Number: 4,927,918
Banks et al.                       [45] Date of Patent: May 22, 1990

[54] ANTIPARASITIC AGENTS

[75] Inventors: Bernard J. Banks, Margate; Michael J. Witty, Dover, both of England

[73] Assignee: Pfizer Inc., New York, N.Y.

[21] Appl. No.: 336,400

[22] Filed: Apr. 11, 1989

[30] Foreign Application Priority Data

Apr. 19, 1988 [GB] United Kingdom ............... 8809232

[51] Int. Cl.$^5$ .............................. C07H 17/08
[52] U.S. Cl. ............................ 536/7.1; 549/268
[58] Field of Search ............... 549/268; 514/450; 536/7.1

[56] References Cited

FOREIGN PATENT DOCUMENTS 0214731 3/1987 European Pat. Off. .
0284176 9/1988 European Pat. Off. .

Primary Examiner—Glennon H. Hollrah
Assistant Examiner—Amelia A. Owens
Attorney, Agent, or Firm—Peter C. Richardson; J. Trevor Lumb; Gregg C. Benson

[57] ABSTRACT

Antiparasitics comprising Avermectin derivatives of formula (I):

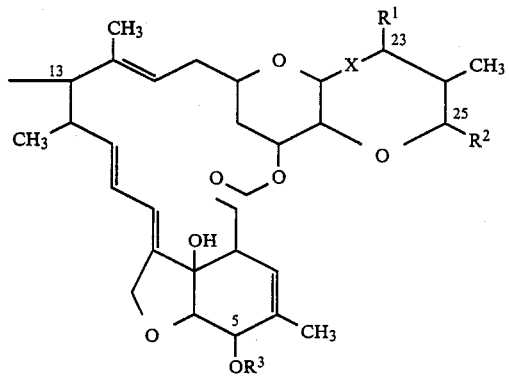

wherein X represents a single or a double bond; $R^1$ is H or OH; provided that when X is a single bond, $R^1$ is H or OH, and when X is a double bond, $R^1$ is absent;

$R^2$ is an alkyl group substituted by one oxo or one or more hydroxy groups or by a single oxygen atom on two adjacent carbon atoms to form an oxirane ring, or $R^2$ is an alkyl group substituted by an alkoxycarbonyl group, said substituents on $R_2$ being attached to either or both a terminal carbon atom and a carbon atom adjacent to a terminal carbon atom of $R^2$; and $R^3$ is H or $CH_3$; or, when $R^2$ is oxo-substituted alkyl, an alkyl acetal or ketal derivative thereof.

17 Claims, No Drawings

ANTIPARASITIC AGENTS

BACKGROUND OF THE INVENTION

This invention relates to antiparasitic agents and in particular to compounds related to the avermectins but having a novel substituent group at the 25-position and to processes for their preparation and compositions thereof.

The avermectins are a group of broad spectrum antiparasitic agents referred to previously as the C-076 compounds. They are produced by fermenting a strain of the microorganism *Streptomyces avermitilis* under aerobic conditions in an aqueous nutrient medium containing inorganic salts and assimilable sources of carbon and nitrogen. The isolation and the chemical structure of the eight individual components which make up the C-076 complex is described in detail in British Patent Specification No. 1573955.

European Patent Applications Nos. 0214731, published Mar. 18, 1987, and 0284176, published Sept. 28, 1988, and U.S. application Ser. No. 249,749, filed Sept. 27, 1988, describe preparation of compounds related to the avermectins but having an unnatural substituent group at the 25-position in place of the isopropyl or sec-butyl group which is present in the naturally occurring avermectins.

SUMMARY OF THE INVENTION

The present invention provides a further series of semi-synthetically derived novel compounds wherein the 25-position substituent is a hydroxy or oxo-substituted alkyl group. The compounds possess a broad spectrum of activity against insect pests, acari, free-living nematodes and parasites affecting humans and animals.

Thus, according to the present invention there are provided compounds having the formula (I):

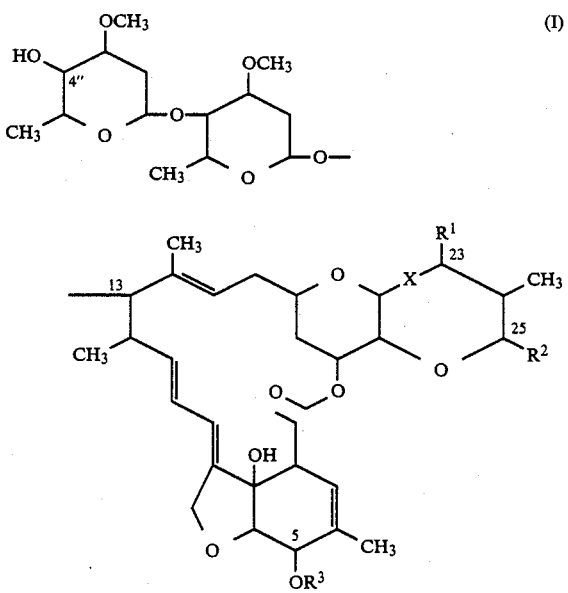

wherein X represents a single or a double bond; $R^1$ is H or OH; provided that when X is a single bond, $R^1$ is H or OH, and when X is a double bond, $R^1$ is absent;

$R^2$ is a $C_1$–$C_6$ alkyl group substituted by one oxo or one or more hydroxy groups or by a single oxygen atom on two adjacent carbon atoms forming an oxirane ring, or $R^2$ is a $C_1$–$C_5$ alkyl group substituted by a ($C_1$–$C_6$ alkoxy)carbonyl group, said substituents on $R_2$ being attached to either or both a terminal carbon atom and a carbon atom adjacent to a terminal carbon atom of $R^2$, $R^3$ is H or $CH_3$; and, in the case where $R^2$ is substituted by oxo, a ($C_1$–$C_4$ alkyl) acetal or ketal derivative thereof.

In the above definition, alkyl groups containing three or more carbon atoms may be straight or branched chain.

Particular examples of compounds wherein $R^2$ is $C_1$–$C_6$ alkyl substituted by oxo include in particular, formyl, acetyl, formylmethyl and 1-methyl-3-oxobutyl derivatives. Examples of compounds wherein $R^2$ is $C_1$–$C_6$ alkyl substituted by hydroxy include in particular, hydroxymethyl, 1-hydroxyethyl, 2-hydroxyethyl, 1,2-dihydroxyethyl and 1-methyl-3-hydroxybutyl derivatives.

Acetal and ketal derivatives include for example 2,2-dimethoxyethyl and 1,1-dimethoxyethyl derivatives of the compounds wherein $R^2$ is formylmethyl or acetyl, respectively. An example of a ($C_1$–$C_6$ alkoxy)carbonyl group is methoxycarbonyl.

The C-076 complex comprises eight distinct but closely related compounds described as C-076 A1*a*, A1*b*, A2*a*, A2*b*, B1*a*, B1*b*, B2*a* and B2*b*. The "a" series of compounds refers to the natural avermectins wherein the 25-substituent is (S)-sec-butyl and the "b" series to those wherein the 25-substituent is isopropyl. The designations "A" and "B" refer to avermectins wherein the 5-substituent is methoxy or hydroxy, respectively, and the numeral "1" refers to avermectins wherein a double bond is present at the 22-23 position, and numeral "2" to avermectins lacking the 22, 23 double bond and having a hydrogen at the 22-position and hydroxy at the 23 position.

In this specification, the "a" and "b" identifiers have been dropped, however, identifiers A1, A2, B1 and B2 have been retained to refer to non-natural avermectins having the structural features corresponding to those of the natural avermectins as noted above.

Particularly preferred compounds according to the invention are the compound of formula (I) where $R^2$ is acetyl, and the ketals thereof. The compound wherein $R^1$ is absent, the 22–23 double bond is present and $R^3$ is hydroxy (25-acetyl-avermectin B1) and the methyl ketal thereof are especially preferred.

DETAILED DESCRIPTION OF THE INVENTION

The compounds of formula (I) are prepared from an avermectin derivative wherein the C-25 substituent is a $C_2$–$C_6$ alkenyl group by a number of different processes, for example as illustrated by the following reaction scheme which shows various chemical transformation reactions which can be performed on the C-25 substituent group:

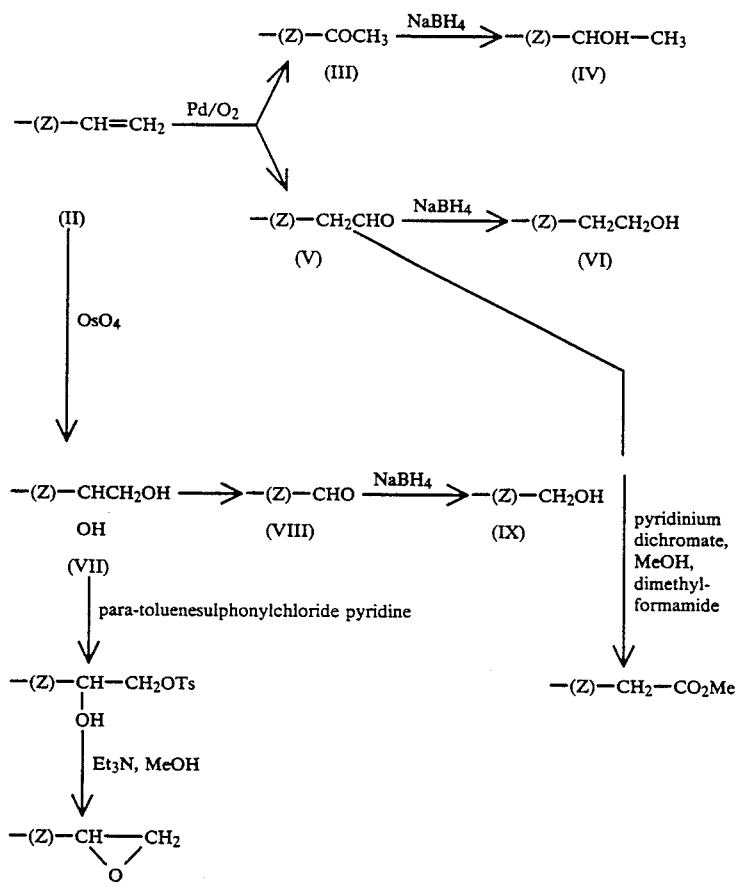

In the above formulae (Z) represents a direct chemical bond or a $C_1$-$C_4$ alkyl group which may be straight or branched-chain.

(a) As illustrated in Scheme 1, compounds of the formula (I) wherein $R^2$ is $C_1$-$C_6$ alkyl substituted by oxo may be prepared from a 25-substituted $C_2$-$C_6$ alkenyl avermectin derivative by oxidation. A variety of reagents are available but we have found that the oxidation may conveniently be performed by stirring a solution of the alkene in an aqueous organic solvent, for example aqueous N,N-dimethylformamide, in the presence of a catalyst, for example using a mixture of palladium chloride and copper chloride, while the reaction mixture is exposed to atmospheric oxygen. After a period of from 4 to 6 hours at room temperature the solution is filtered and the product wherein $R^2$ is of formula (III) or (V) is isolated by solvent extraction. Further purification, if required, is achieved using conventional chromatographic techniques.

Using this process, for example, oxidation of an 25-ethenyl-avermectin yields the corresponding compounds of formula I wherein $R^2$ is acetyl or formylmethyl. The ratio of these two components will vary according to the starting material used and the precise reaction conditions employed.

(b) As an alternative to the above, the oxidation step may also be performed in the presence of osmium tetroxide to yield the corresponding diol (VII). This reaction is generally achieved by stirring the reactants in an inert organic solvent, for example tertiary butanol, at room temperature for several hours. The product is isolated and purified by conventional procedures. The diol product may then be subjected to a further oxidation step, for example by treatment with sodium metaperiodate, to effect cleavage of the gem-diol and to yield the aldehyde product wherein $R^2$ is of formula (VIII).

Osmium tetroxide is toxic and it is preferred to conduct the oxidation with this reagent using a small amount of osmium tetroxide in the presence of N-methyl morpholine oxide which regenerates the osmium tetroxide as it is consumed. The reaction may be carried out in an aqueous acetone solvent. This procedure allows the osmium tetroxide to be used in a catalytic amount which is much less than the stoichiometric amount required to oxidise the alkene group.

(c) Compounds of formula (I) wherein $R^2$ is $C_1$-$C_6$ alkyl substituted by one or more hydroxy groups may be obtained by osmium tetroxide oxidation of the alkene as described above, or by reduction of the aldehyde or ketone products. The reduction step is conveniently achieved by treatment with, for example, a borohydride reducing agent such as sodium borohydride, in methanol solution for 2 or 3 hours at room temperature. The hydroxy product wherein $R^2$ is of formula (IV), (VI) or (IX) is then isolated and purified by conventional procedures as previously described. Thus, for example reduction of a 25-acetyl avermectin yields the corresponding 25-(1-hydroxyethyl) derivative.

(d) Compounds of formula (I) wherein $R^2$ is $C_1$-$C_6$ alkyl substituted by a single oxygen atom on two adjacent carbon atoms to form an oxirane ring may be obtained by cyclising the corresponding compound having hydroxyl substituents on the adjacent carbon atoms.

This cyclisation may be carried out by firstly treating the dihydroxy compound with para-toluene sulphonyl chloride in the presence of a base such as pyridine, generally at room temperature to give a monotosylate from which the oxirane product may be obtained by treatment with a suitable base such as triethylamine.

(e) Compounds of formula (I) wherein $R^2$ is a $C_1$–$C_5$ alkyl substituted by a ($C_1$–$C_4$ alkoxy)carbonyl group may be obtained by oxidising the corresponding compound substituted by oxo on a terminal carbon atom (an aldehyde), formula (V), in the presence of an alcohol. A suitable oxidising agent for this purpose is pyridinium dichromate and the reaction may be conducted by stirring the oxo compound (V) with pyridinium dichromate and a solvent such as dimethylformamide with the appropriate alcohol (such as methanol to give the methyl ester) at room temperature. The ester product may be isolated by evaporating the reaction mixture to dryness, extracting the residue with ethyl acetate and purifying by chromatography.

When the avermectin used has a hydroxy substituent at the 5-position (a B avermectin) the above-described oxidation of the aldehyde group generally results in simultaneous oxidation of the 5-hydroxy substituent to produce a 5-keto avermectin derivative. The 5-keto group may be reduced by sodium borohydride in known manner to yield the B avermectin derivative.

Alternatively the hydroxy group at the 5-position of the avermectin may be protected, for example by forming the tertiary butyl dimethyl silyl ether, followed by transformation of the avermectin at the 25-position as described above, and removal of the protective group for example by treatment with para-toluene sulphonic acid in methanol at room temperature.

All the above transformation reactions employ conventional reagents and appropriate conditions for their use will be known to those skilled in the art.

The starting compounds of formula (I) wherein $R^2$ is an alkenyl group may be obtained by fermentation by adding an appropriate unsaturated carboxylic acid to a fermentation of an avermectin producing organism as described in EP-A-No. 0214731 or our European patent application No. 88300353.5 or British patent application No. 8726730. Thus, for example, feeding 2-methyl-pent-4-enoic acid provides the compound of formula (I) wherein $R^2$ is 1-methyl-but-3-enyl. Alternatively, they may be obtained from the corresponding C-25 alkylthioalkyl avermectin derivative as described in our co-pending U.K. application No. 8807280. Thus, for example, oxidation of a 25-(1-methylthioethyl)avermectin derivative followed by thermal elimination yields the corresponding 25-ethenyl-avermectin starting materials.

As previously mentioned the compounds of the invention are highly active antiparasitic agents having particular utility as anthelmintics, ectoparasiticides, insecticides, acaricides and animal growth promotants.

Thus the compounds are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites which can infect humans including gastro-intestinal parasites such as Ancylostoma, Necator, Ascaris, Strongyloides, Trichinella, Capillaria, Trichuris, Enterobius and parasites which are found in the blood or other tissues and organs such as filiarial worms and the extra intestinal stages of Strongyloides and Trichinella.

The compounds are also of value in treating ectoparasite infections including in particular arthropod ectoparasites of animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against insect pests of stored grain and of agricultural plants such as spider mites, aphids, caterpillars, fire ants, termites and against migratory orthopterans such as locusts.

The compounds of formula (I) are administered as a formulation appropriate to the specific use envisaged and to the particular species of host animal being treated and the parasite or insect involved. For use as an anthelmintic the compounds are preferably administered by injection, either subcutaneously or intramuscularly, alternatively they may be administered orally in the form of a capsule, bolus, tablet or liquid drench, or they may be administered as a pour-on formulation or as an implant. Such formulations are prepared in a conventional manner in accordance with standard veterinary practice. Thus injectable formulations may be prepared in the form of a sterile solution or emulsion. Capsules, boluses or tablets may be prepared by mixing the active ingredient with a suitable finely divided diluent or carrier, additionally containing a disintegrating agent and/or binder such as starch, lactose, talc, or magnesium stearate. A drench formulation may be prepared by dispersing the active ingredient in an aqueous solution together with dispersing or wetting agents. These formulations will vary with regard to the weight of active compound depending on the species of host animal to be treated, the severity and type of infection and the body weight of the host. Generally for oral or parenteral administration, a dose of from about 0.001 to 10 mg per kg, preferably 0.01 to 1 mg/kg of animal body weight given as a single dose or ine divided doses for a period of from 1 to 5 days will be satisfactory but of course there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests, the compounds are applied as sprays, dusts, emulsions pour-on formulations and the like in accordance with standard agricultural practice.

For use as a growth promotant or for improving the lean meat to fat ratio in farm or domestic animals, the compounds may be administered with the animal feedstuff or drinking water. Alternatively they may be administered orally in the form of a capsule, bolus, tablet or liquid drench, or parenterally by injection or as an implant. Such formulations are prepared in a conventional manner in accordance with standard veterinary practice.

For human use the compounds are administered as a pharmaceutically acceptable formulation in accordance with normal medical practice.

The invention is illustrated by the following Examples in which analytical data were obtained by the following procedures.

Fast atom bombardment (FAB) mass spectrometry was performed on a VG Model 7070E mass spectrometer using a sample matrix of glycerol, thioglycerol, water and sodium chloride. Electron impact (EI) mass spectrometry was performed using a VG model 7070E mass spectrometer. m/z values are quoted for the principal fragments. $^1$H Nuclear magnetic resonance (NMR) spectral data were obtained on a Nicolet QE 300 or General Electric GN 500 spectrometer with a sample concentration of 5 mg/ml in deuteriochloroform. The chemical shifts are given in parts per million relative to tetramethylsilane.

Preparation of compounds according to the invention will now be described by way of illustration in the following Examples.

EXAMPLE 1

25-(1-Methyl-3-oxobutyl)-avermectin A2 (formula I; $R^1$=OH, 22,23-double bond absent, $R^2$=—CH(CH$_3$)CH$_2$COCH$_3$, $R^3$=CH$_3$).

A mixture of palladium chloride (100 mg), cuprous chloride (100 mg) and 25-(1-methylbut-3-enyl)-avermectin A2 (250 mg) in 10% aqueous N,N-dimethylformamide was stirred vigorously at room temperature for four hours while exposed to the atmosphere. The reaction mixture was then evaporated to dryness and the residue taken up in methanol. The solution was filtered and evaporated to yield the crude product which was purified by reverse-phase high pressure liquid chromatography on a Dynamax (trade mark) —60A C18 column eluting with 20% aqueous methanol. Evaporation of the appropriate fractions gave the title product as a white solid (209 mg).

FAB mass spectrometry: (M+Na$^+$) observed at m/z 955 (theoretical 955).

EI mass spectrometry: 626, 594, 576, 351, 333, 315, 249, 239, 219, 179, 155, 145, 113, 95, 87.

$^1$H NMR spectral data were as expected for an A2 avermectin with characteristic peaks for the C-25 side-chain at 2.6 (3H, m, CHCH$_2$), 2.2 (3H, s, COCH$_3$), 0.95 (3H, d, CHCH$_3$).

EXAMPLE 2

25-(1-Methyl-3-hydroxybutyl)-avermectin A2 (formula I; $R^1$=OH, 22,23-double bond absent, $R_2$=—CH(CH$_3$)CH$_2$CH(OH)CH$_3$, R3=CH$_3$).

A mixture of sodium borohydride (3 mg) and 25-(1-methyl-3-oxobutyl)-avermectin A2 (25 mg) in methanol (2 ml) was stirred at room temperature for 5 minutes. The reaction mixture was then partitioned between dichloromethane and saturated aqueous sodium bicarbonate. The organic phase was dried and evaporated and the residue retaken up in aqueous methanol. The solvent was evaporated to yield the required product as a white solid (22 mg). Analysis by reverse phase high pressure liquid chromatography showed a mixture of diastereomers in a 4:5 ratio which could be resolved further by high pressure liquid chromatography.

FAB mass spectrometry: (M+Na$^+$) observed at m/z 957 (theoretical 957).

EI mass spectrometry: 628, 358, 335, 317, 179, 157, 145, 113, 99, 87.

$^1$H NMR spectral data were as expected for an A2 avermectin with characteristic peaks for the C-25 side-chain at 1.6 (2H, m, CH$_2$), 1.3 (3H, d, CH(OH)CH$_3$), 0.95 (3H, d, CHCH$_3$).

EXAMPLE 3

25-Acetyl-avermectin A2 (formula I; $R^1$=OH, 22,23-double bond absent, $R^2$=—COCH$_3$, $R^3$=CH$_3$).

A mixture of palladium chloride (5 mg), cupric chloride (20 mg) and 25-ethenyl-avermectin A2 (50 mg) in 10% aqueous N,N-dimethylformamide (2 ml) was stirred vigorously at room temperature for 2 hours while exposed to the atmosphere. The reaction mixture was then poured into a mixture of water (2 ml) and diethyl ether (20 ml). The ether layer was separated, dried (Na$_2$SO$_4$) and evaporated to give the crude product as an oil which was purified by reverse-phase high pressure liquid chromatography on a 2.5 cm diameter Beckman Ultrasphere-ODS (trade mark) column eluting with a mixture of acetonitrile, methanol and water (40:30:30). The product was obtained following evaporation of the appropriate fractions as a white solid (25.5 mg).

FAB mass spectrometry: (M+Na$^+$) observed at m/z 913 (theoretical 913).

EI mass spectrometry: 584, 309, 291, 275, 257, 225, 207, 197, 179, 155, 145, 127, 113, 111, 95, 87.

The $^1$H NMR spectral data were as expected for an A2 avermectin with characteristic peaks for the C-25 side-chain at 2.28 (3H, s, —COCH$_3$).

EXAMPLE 4

25-(1-Hydroxethyl)-avermectin A2 (formula I; $R^1$=OH, 22,23-double bond absent $R^2$=—CH(OH)CH$_3$, $R^3$=CH$_3$).

A mixture of sodium borohydride (1 mg) and 25-acetylavermectin A2 (12 mg) in methanol (2 ml) was stirrd at room temperature for 15 minutes. The reaction mixture was passed through a short column of silica and the eluate evaporated to yield the crude product as a 7:1 mixture of diastereoisomers. The major component was isolated by reverse-phase high pressure liquid chromatography on a 1.25 cm diameter Beckman Ultrasphere-ODS (trade mark) column eluting with a mixture of acetonitrile, methanol and water (20:45:35). The title product was obtained following evaporation of the appropriate fractions as a white solid (5 mg).

FAB mass spectrometry: (M+Na$^+$) observed at m/z 915 (theoretical 915).

EI mass spectrometry: 586, 311, 293, 275, 257, 227, 209, 199, 181, 179, 157, 145, 127, 113, 111, 95, 87.

The $^1$H NMR spectral data were as expected for an A2 avermectin with characteristic peaks for the C-25 side-chain at 1.42 (3H, d, CH(OH)CH$_3$).

EXAMPLES 5-8

25-Acetyl-avermectin B1,
25-Formylmethyl-avermectin B1,
25-(2,2-Dimethoxyethyl)-avermectin B1, and
25-(1,1-Dimethoxyethyl)-avermectin B1 (formula I; $R^1$=absent, 22,23-double bond present, $R^3$=H, $R^2$=—COCH$_3$, —CH$_2$CHO, —CH$_2$CH(OCH$_3$)$_2$ and —C(OCH$_3$)$_2$CH$_3$ respectively).

A mixture of palladium chloride (200 mg), cuprous chloride (200 mg) and 25-ethenyl-avermectin B1 (500 mg) in 10% aqueous N,N-dimethylformamide (10 ml) was stirred vigorously at room temperature for 1 hour while exposed to the atmosphere. The reaction mixture was poured into methanol (200 ml) and allowed to stand overnight. The solvents were evaporated and the residue partitioned between diethyl ether (200 ml) and water (50 ml). The ether layer was separated, dried ($Na_2SO_4$) and evaporated to give the crude product (500 mg) as a yellow solid containing a mixture of the 25-acetyl and 25-formylmethyl derivatives together with their methanol acetal and ketal derivatives. This material was combined with the crude product obtained from two further runs and the mixture purified by reverse-phase high pressure liquid chromatography on a Dynamax-60A C18 (trade mark) column eluting with a mixture of methanol and water (70:30). Evaporation of the appropriate fractions gave the following products as white solids:

25-Acetyl avermectin B1 (230 mg).

FAB mass spectrometry: $(M+Na^+)$ observed at m/z 881 (theoretical 881).

EI mass spectrometry 554, 357, 291, 261, 257, 243, 226, 207, 197, 179, 171, 155, 153, 145, 127, 113, 111, 105, 95, 87.

The $^1H$ NMR spectral data were as expected for a B1 avermectin with characteristic peaks for the C-25 side-chain at 2.35 (3H, s, $COCH_3$).

25-Formylmethyl-avermectin B1 (69 mg).

FAB mass spectrometry: $(M+Na^+)$ observed at m/z 881 (theoretical 881).

EI mass spectrometry: 442, 291, 261, 257, 207, 179, 155, 145, 127, 113, 111, 95, 87.

The $^1H$ NMR spectral data were as expected for a B1 avermectin with characteristic peaks for the C-25 side-chain at 9.935 (1H, t, $-CH_2CHO$).

25-(2,2-Dimethoxyethyl)-avermectin B1 (26 mg).

FAB mass spectrometry: $(M+Na^+)$ observed at m/z 927 (theoretical 927).

EI mass spectrometry: 566, 337, 321, 305, 181, 163, 145, 113, 95, 87.

The $^1H$ NMR spectral data were as expected for a B1 avermectin with characteristic peak for the C-25 side-chain at 1.714 (1H, ddd, $-CH_2CH(OCH_3)_2$), 1.997 (1H, ddd, $-CH_2CH(OCH_3)_2$), 3.33 and 3.36 (6H, s and s, $-CH_2CH(OCH_3)_2$), 4.748 (1H, dd, $-CH_2CH(OCH_3)_2$).

25-(1,1-Dimethoxyethyl)-avermectin B1 (70 mg).

FAB mass spectrometry: $(M+Na^+)$ observed at m/z 927 (theoretical 927).

EI mass spectrometry: 568, 549, 305, 221, 193, 169, 145, 113, 95, 87.

The $^1H$ NMR spectral data were as expected for a B1 avermectin with characteristic peaks for the C-25 side-chain at 1.39 (3H, s, $C(OCH_3)_2CH_3$), 3.25 and 3.27 (6H, s and s, $C(OCH_3)_2CH_3$).

EXAMPLE 9

25-(1-Hydroxyethyl)-avermectin B1 (formula I; $R^1$ absent, 22,23-double bond present, $R^2=-CH(OH)CH_3$, $R^3=H$).

A mixture of sodium borohydride (1 mg) and 25-acetylavermectin B1 (30 mg) in methanol (1 ml) was stirred at room temperature for 10 minutes. The reaction mixture was partitioned between diethyl ether (20 ml) and water (5 ml). The ether layer was separated, dried ($Na_2SO_4$) and evaporated to give the crude product as a 4:1 mixture of diastereoisomers. The major component was isolated by reverse-phase high pressure liquid chromatography on a 1.25 cm diameter Beckman Ultrasphere - ODS (trade mark) column eluting with a mixture of water and methanol (28:72). The product was obtained following evaporation of the appropriate fractions as a white solid (15 mg).

FAB mass spectrometry: $(M+Na^+)$ observed at m/z 883 (theoretical 883).

EI mass spectrometry: 554, 293, 261, 257, 209, 181, 157, 145, 127, 113, 111, 95, 87.

The $^1H$ NMR spectral data were as expected for a B1 avermectin with characteristic peaks for the C-25 side-chain at 1.41 (3H, d, $-CH(OH)CH_3$).

EXAMPLE 10

25-(2-Hydroxyethyl)-avermectin B1 (formula I; $R^1$ absent, 22,23-double bond present, $R^2=-CH_2CH_2OH$, $R^3=H$).

A mixture of sodium borohydride (2 mg) and 25-formylmethyl-avermectin B1 (45 mg) in methanol (2 ml) was stirred at room temperature for 10 minutes. The reaction mixture was partitioned between diethyl ether (40 ml) and water (10 ml). The ether layer was separated, dried ($Na_2SO_4$) and evaporated. The crude product was purified by reverse-phase high pressure liquid chromatograph on a 1.25 cm Ultrasphere-ODS (trade mark) column eluting with a mixture of water and methanol (30:70). The product was obtained as a white solid following evaporation of the appropriate fractions (20 mg).

FAB mass spectrometry: $(M+Na^+)$ observed at m/e 883 (theoretical 883).

EI mass spectrometry: 293, 275, 257, 243, 225, 213, 209, 145, 127, 113, 109, 95, 87.

The $^1H$ NMR spectral data were as expected for a B1 avermectin with characteristic peaks for the C-25 side-chain at 1.80 (1H, m, $-CH_2CH_2OH$), 2.038 (1H, m, $-CH_2CH_2OH$), 3.869 (2H, m, $-CH_2CH_2OH$).

EXAMPLE 11

25-(1,2-Dihydroxyethyl)-avermectin A2 (formula I; $R^1=OH$, 22,23-double bond absent, $R^2=-CH(OH)CH_2OH$, $R^3=CH_3$).

A solution of 25-ethenyl-avermectin A2 (100 mg), osmium tetroxide (60 microlitres of a 2.5% solution in t-butanol) and N-methylmorpholine oxide (20 mg) in a mixture of acetone (9 ml) and water (1 ml) was stirred at room temperature for four hours. The reaction mixture was then partitioned between diethyl ether (40 ml) and water (10 ml). The organic layer was separated, dried ($Na_2SO_4$) and evaporated. The crude product was purified by reverse-phase high pressure liquid chromatography on a 1.25 cm diameter Beckman Ultrasphere-ODS (trade mark) column eluting with water and methanol (33:67). The product was obtained as a white solid following evaporation of the appropriate fractions (48 mg).

FAB mass spectrometry: $(M+Na^+)$ observed at m/z 931 (theoretical 931).

EI mass spectrometry: 327, 309, 215, 179, 145, 135, 127, 113, 105, 95, 87.

The $^1H$ NMR spectral data were as expected for an A2 avermectin with characteristic peaks for the C-25 side-chain at 3.87 (1H, m, $-CH(OH)CH_2OH$), 3.85 (1H, m, $-CH(OH)CH_2OH$), 3.76 (1H, m, $-CH(OH)CH_2OH$).

EXAMPLE 12

25-Formyl-avermectin A2 (formula I; $R^1$=OH, 22,23-double bond absent, $R^2$=CHO, $R^3$=CH$_3$).

A solution of 25-ethenyl-avermectin A2 (100 mg), osmium tetroxide (60 microlitres of a 2.5% solution in t-butanol) and N-methylmorpholine oxide (20 mg) in a mixture of acetone (9 ml) and water (1 ml) was stirred at room temperature for 4 hours. Sodium metaperiodate (50 mg) was then added and the mixture stirred for a further 30 minutes. The mixture was concentrated to a small volume and partitioned between diethyl ether (40 ml) and water (10 ml). The organic layer was separated, dried (Na$_2$SO$_4$) and evaporated. Two further reactions starting with 250 mg and 575 mg of 25-ethenyl-avermectin were performed following the same procedure. The crude products were combined and purified by reverse-phase high pressure liquid chromatography on a Dynamax-60A (trade mark) column eluting with a mixture of water and methanol (30:70). The product was obtained as a white solid following evaporation of the appropriate fractions (300 mg).

FAB mass spectrometry: (M+Na$^+$) observed at m/z 899 (theoretical 899).

EI mass spectrometry: 570, 538, 327, 295, 277, 211, 183, 145, 127, 113, 95, 87.

The $^1$H NMR spectral data were as expected for an A2 avermectin with characteristic peaks for the C-25 side-chain at 9.68 (1H, d, CHO).

EXAMPLE 13

25-Hydroxymethyl-avermectin A2 (formula I; $R^1$=OH, 22,23-double bond absent, $R^2$=—CH$_2$OH, $R^3$=CH$_3$).

A mixture of sodium borohydride (2 mg) and 25-formyl-avermectin A2 (40 mg) in methanol (1 ml) was stirred at room temperature for 2 hours. The reaction mixture was partitioned between diethyl ether (20 ml) and water (5 ml). The ether layer was separated, dried (Na$_2$SO$_4$) and evaporated. The crude product was purified by reverse-phase high pressure liquid chromatography on a 1.25 cm diameter Beckman ODS (trade mark) column eluting with a mixture of water and methanol (33:67). The product was obtained as a white solid following evaporation of the appropriate fractions (20 mg).

FAB mass spectrometry: (M+Na$^+$) observed at m/z 901 (theoretical 901).

EI mass spectrometry: 572, 297, 279, 213, 179, 161, 145, 143, 127, 113, 95, 87.

The $^1$H NMR spectral data were as expected for an A2 avermectin with characteristic peaks for the C-25 side-chain at 3.83 (2H, —CH$_2$OH).

EXAMPLE 14

25-Formyl-avermectin B1 (formula I; $R^1$=absent, 22,23-double bond present, $R^2$=—CHO, $R^3$=H).

A solution of 25-ethenyl-avermectin B1 (270 mg), osmium tetroxide (162 microlitres of a 2.5% solution in t-butanol) and N-methylmorpholine oxide (54 mg) in a mixture of acetone (22.5 ml) and water (2.5 ml) was stirred at room temperature for 6 hours. Further osmium tetroxide (162 microlitres of a 2.5% solution in t-butanol) and N-methylmorpholine oxide (54 mg) was added and the mixture stirred for 1 hour. Sodium metaperiodate (270 mg) was then added and the mixture stirred for a further 30 minutes. The mixture was concentrated to a small volume and partitioned between diethyl ether (100 ml) and water (25 ml). The organic layer was separated, dried (Na$_2$SO$_4$) and evaporated. The crude product (160 mg) was purified by reverse-phase high pressure liquid chromatography on a 21.2 mm diameter Du Pont Zorbax (trade mark) column eluting with a mixture of water and methanol (30:70). The product was obtained as a white solid following evaporation of the appropriate fractions (6 mg).

FAB mass spectrometry: (M+Na$^+$) observed at m/z 867 (theoretical 867).

EI mass spectrometry: 538, 428, 277, 261, 257, 193, 165, 145, 127, 113, 111, 95, 87.

The 1H NMR spectral data were as expected for a B1 avermectin with characteristic peaks for the C-25 side-chain at 9.76 (1H, d, CHO).

EXAMPLE 15

25-Methoxycarbonylmethylavermectin B1 (formula I; $R^1$=absent, 22,23-double bond present, $R^2$=—CH$_2$CO$_2$Me, $R^3$=H).

A mixture of 25-formylmethyl-avermectin B1 (9 mg), methanol (24 microlitres), dimethylformamide (0.5 ml, anhydrous) and pyridinium dichromate (22.5 mg) was stirred for 4 hours and then evaporated to dryness. The residue was taken up in ethyl acetate (5 ml) and passed through a silica Sep-Pak (Trade Mark) chromatography column. The eluate was evaporated and the residue was taken up in methanol (5 ml) and sodium borohydride (1 mg) added. The mixture was allowed to stand for 15 minutes and then evaporated to dryness to give the crude product which was purified by reverse-phase high pressure liquid chromatography on a 10 mm diameter Beckman ODS (trade mark) column eluting with a mixture of water and methanol (30:70). The product was obtained as a white solid following evaporation of the appropriate fractions (0.26 mg).

FAB mass spectrometry: (M+Na$^+$) observed at m/z 911 (theoretical 911).

EI mass spectrometry: 582, 321, 261, 257, 237, 209, 185, 145, 127, 113, 111, 95, 87.

The 1$_H$ NMR spectral data were as expected for a B1 avermectin with a characteristic peak for the methyl moiety of the C-25 side-chain at 3.76 (3H, s, —CH$_2$CO$_2$CH$_3$).

EXAMPLE 16

25-Oxiranyl-avermectin A2 (formula I; $R^1$=OH, 22,23-double bond absent,

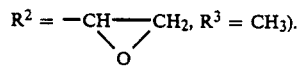

$R^2$ = —CH—CH$_2$, $R^3$ = CH$_3$).

A solution of 25-(1,2-dihydroxyethyl)-avermectin A2 (17 mg), para-toluenesulphonyl chloride (85 mg) and 4-dimethylaminopyridine (0.5 mg) in pyridine (1 ml) was stirred at room temperature for 24 hours. The reaction mixture was diluted with ether (20 ml) and then washed with water (20 ml), hydrochloric acid (0.2 N, 20 ml), saturated sodium hydrogen carbonate solution (20 ml) and brine (20 ml). The organic layer was then dried (Na$_2$SO$_4$) and evaporated. The crude product was purified by reverse-phase high pressure liquid chromatography on a 10 mm diameter Beckman ODS (trade mark) column eluting with a mixture of water and methanol (30:70). Combination and evaporation of appropriate fractions gave a mono-para-toluenesulphonylated-avermectin which was dissolved in methanol (3 ml) containing triethylamine (0.1 mg). The mixture was allowed to stand at room temperature for 30 hours and then evaporated. The crude product was dissolved in dichloromethane and applied to a silica Sep-Pak (trade mark) chromatography column. Elution with ethyl acetate and evaporation of the elate gave the crude product which was purified by reverse-phase high pressure liquid chromatography on a 10 mm diameter Beckman ODS (trade mark) column eluting with a mixture of water and methanol (25:75). The product was obtained as a white solid following evaporation of the appropriate fractions (1.5 mg).

FAB mass spectrometry: (M+Na+) observed at 913 (theoretical 913).

EI mass spectrometry: 584, 309, 291, 289, 275, 257, 225, 207, 197, 179, 155, 145, 127, 113, 111, 95, 87.

The $^1$H NMR spectral data were as expected for an A2 avermectin with characteristic peaks for the C-25 side-chain at

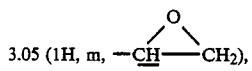

3.05 (1H, m, —CH——CH$_2$),

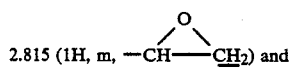

2.815 (1H, m, —CH——CH$_2$) and

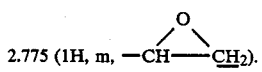

2.775 (1H, m, —CH——CH$_2$).

- Activity Data

Anthelmintic Activity

Anthelmintic activity was evaluated against *Caenorhabditis elegans* using the in vitro screening test described by K. G. Simpkin and G. L. Coles in Parasitology, 1979, 79, 19, with a well concentration of 1 microgram per ml.

Insecticidal Activity

Activity against the larval stage of the blowfly *Lucilia cuprina* (Q strain) is demonstrated using a standard procedure in which first instar larvae are kept in contact with filter paper treated with test compound. The test compound is first applied to the paper as an acetone solution to give a concentration of the test compound of 1 milligram per square metre. The treated filter papers are then placed into tubes containing 1 ml of newborn calf serum and the first instars are added. The tubes are examined after 24 hours and the % of larvae killed recorded.

The compounds of the invention are active in the above tests, with, for most compounds, 100% of the worms or larvae killed at the concentration of test compound stated.

We claim:

1. A compound of formula (I):

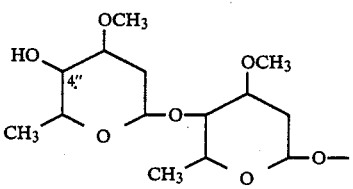

(I)

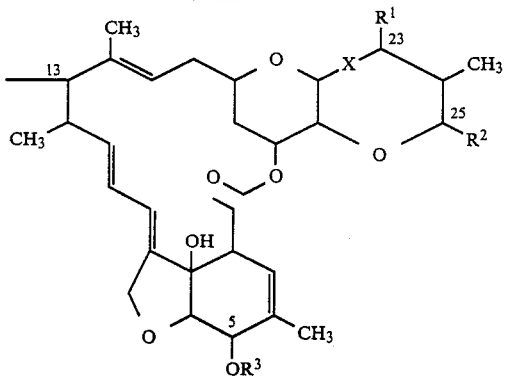

wherein X represents a single or a double bond; $R^1$ is H or OH; provided that when X is a single bond, $R^1$ is H or OH, and when X is a double bond, $R^1$ is absent; $R^2$ is a $C_1$–$C_6$ alkyl group substituted by one oxo or one or more hydroxy groups or by a single oxygen atom on two adjacent carbon atoms to form an oxirane ring, or $R^2$ is a $C_1$–$C_5$ alkyl group substituted by a ($C_1$–$C_6$ alkoxy) carbonyl group, said substituents on $R_2$ being attached to either or both a terminal carbon atom and a carbon atom adjacent to a terminal carbon atom of $R^2$; and $R^3$ is H or CH$_3$; or, when $R^2$ is substituted by oxo, a ($C_1$–$C_4$ alkyl) acetal or ketal derivative thereof.

2. A compound according to claim 1 in which $R^2$ is $C_1$–$C_6$ alkyl group substituted by one or more hydroxy groups, by oxo or by a ($C_1$–$C_4$ alkyl) acetal or ketal group.

3. A compound according to claim 2 wherein $R^2$ is a formyl, acetyl, formylmethyl or 1-methyl-3-oxobutyl group.

4. A compound according to claim 2 wherein $R^2$ is a 2, 2-dimethoxyethyl or 1, 1-dimethoxyethyl group.

5. A compound according to claim 2 wherein $R^2$ is a hydroxymethyl, 1hydroxyethyl, 2-hydroxyethyl, 1, 2-dihydroxyethyl or 1-methyl-3hydroxybutyl group.

6. A compound according to claim 1 wherein $R^2$ is a $C_{1-5}$ alkyl group substituted by a methoxycarbonyl or a $C_{1-6}$ alkyl group substituted by a single oxygen atom on two adjacent carbon atoms to form an oxirane ring.

7. A compound according to claim 2 wherein $R^3$ is H; X represents a double bond; and $R^1$ is absent.

8. A compound according to claim 3 wherein X is a double bond; $R^1$ is absent; and $R^3$ is H.

9. The compound according to claim 8 wherein $R^2$ is acetyl.

10. A compound according to claim 3 wherein X is a single bond; $R^1$ is OH; and $R^3$ is CH$_3$.

11. The compound according to claim 10 wherein $R^2$ is acetyl.

12. A compound according to claim 4 wherein $R^3$ is H; X represents a double bond; and $R^1$ is absent.

13. The compound according to claim 12 wherein $R^2$ is 1, 1-dimethoxy ethyl.

14. A composition for the treatment and prevention of parasitic infections in humans and animals which comprises an antiparasitic amount of a compound of claim 1 together with an inert diluent or carrier.

15. A composition according to claim 14 in the form of a liquid drench or an oral or injectable formulation.

16. A composition according to claim 14 in the form of an animal feedstuff or a premix or supplement for addition to animal feed.

17. A method of treating parasite infections or infestations which comprises contacting the organism responsible for said infection or infestation or the location of said organism with an antiparasitic amount of a compound according to claim 1.

* * * * *